US009545429B1

(12) United States Patent
Kaline

(10) Patent No.: US 9,545,429 B1
(45) Date of Patent: Jan. 17, 2017

(54) HOMEOPATHIC FORMULATIONS

(75) Inventor: Daniel J. Kaline, Grand Rapids, MI (US)

(73) Assignee: BIOLYTE LABORATORIES, LLC, Grand Rapids, MI (US)

( * ) Notice: Subject to any disclaimer, the term of this patent is extended or adjusted under 35 U.S.C. 154(b) by 722 days.

(21) Appl. No.: 13/225,429

(22) Filed: Sep. 3, 2011

(51) Int. Cl.
| | |
|---|---|
| A61K 33/26 | (2006.01) |
| A61K 36/899 | (2006.01) |
| A61K 36/06 | (2006.01) |
| A61K 33/38 | (2006.01) |
| A61K 33/36 | (2006.01) |
| A61K 33/00 | (2006.01) |
| A61K 36/282 | (2006.01) |
| A61K 36/33 | (2006.01) |
| A61K 33/42 | (2006.01) |
| A61K 36/886 | (2006.01) |
| A61K 36/28 | (2006.01) |
| A61K 36/00 | (2006.01) |

(52) U.S. Cl.
CPC .............. *A61K 36/00* (2013.01); *A61K 33/00* (2013.01)

(58) Field of Classification Search
CPC ........ A61K 33/38; A61K 33/42; A61K 45/06; A61K 36/42; A61K 36/88; A61K 33/36; A61K 36/71; A61K 33/26; A61K 33/00
USPC ...................................................... 424/600
See application file for complete search history.

(56) References Cited

U.S. PATENT DOCUMENTS

| | | | |
|---|---|---|---|
| 5,006,338 A | 4/1991 | Luenemann | |
| 5,997,876 A | 12/1999 | Shikhashvili et al. | |
| 6,146,639 A | 11/2000 | Merich | |
| 6,447,788 B1 | 9/2002 | Strathausen | |
| 6,770,263 B1 | 8/2004 | Brucker | |
| 7,229,648 B2 | 6/2007 | Dreyer | |
| 7,781,429 B2 | 8/2010 | Schwarz et al. | |
| 7,871,647 B1 | 1/2011 | Paradise | |
| 2006/0165812 A1* | 7/2006 | Charron | 424/600 |
| 2007/0212434 A1* | 9/2007 | Day et al. | 424/762 |
| 2008/0038219 A1* | 2/2008 | Mosbaugh et al. | 424/74 |
| 2009/0232904 A1* | 9/2009 | Quinto et al. | 424/618 |
| 2011/0038949 A1* | 2/2011 | Oswal et al. | 424/602 |

FOREIGN PATENT DOCUMENTS

| | | |
|---|---|---|
| GB | 2311009 | 9/1997 |

OTHER PUBLICATIONS

Painazol Pain Relief Marketing Information (marketing start date: May 20, 2010).*
Berrebi et al., Treatment of pain due to unwanted lactation with a homeopathic preparation given in the immediate post-partum period, 30 J Gynecol Obstet Biol Reprod (Paris) 353-57 (2001) (English Abstract Provided).
Canadian Intellectual Property Office, Nov. 4, 2011 Search Report for App. No. 2518965.
Cordova et al., Protective properties of butanolic extract of the *Calendula officinalis* L. (marigold) against lipid peroxidation of rat liver microsomes and action as free radical scavenger, 7 Redox Rep 95-102 (2002).
Dr. Frank's Joint & Muscle Pain Relief product information, retrieved from https://www.drfrankspainrelief.com/formula.php on Aug. 19, 2011.
USPTO, Jun. 9, 2005 Examiner-Initiated Interview Summary for Application No. 10797009.
GMI's PainMed product information, retrieved from http://gmipainmed.com/PAIN_MED_ACTIVE_INGREDIENTS.html on Aug. 19, 2011.
USPTO, Sep. 24, 2004 PCT International Search Report for PCT/US04/05231.
EPICURE product label.
Friese et al., The homeopathic treatment of otitis media in children—comparisons with conventional therapy, 35 International Journal of Clinical Pharmacology and Therapeutics 296-301 (1997) (last page missing).
HomeopathyHome.com web pages, retrieved through web.archive.org website.
911 Stress Control product information website, retrieved through web.archive.org website.
USPTO, Jun. 21, 2005 Office Action (Non-Final Rejection) of U.S. Appl. No. 10/797,009.
Knuesel et al., Arnica montana gel in osteoarthritis of the knee: an open, multicenter clinical trial, 19 Adv Ther 209-18 (2002).
Kumar et al, Anti-inflammatory and analgesic activity of Indian *Hypericum perforatum* L., 39 Indian J Exp Biol 339-43 (2001).
Painazol product information, retrieved from http://www.painazol.com/?ssid=0e1d611447ad692e7c278fc08a2026b0 on Aug. 19, 2011.
Rhumatol product information, retrieved from http://www.rhumatol.com/?ssid=0e1d611447ad692e7c278fc08a2026b0 on Aug. 19, 2011.
Traumeel product label.
Van Haselen et al., A randomized controlled trial comparing topical piroxicam gel with a homeopathic gel in osteoarthritis of the knee, 39 Rheumatology 714-19 (2000).

* cited by examiner

*Primary Examiner* — Brian-Yong Kwon
*Assistant Examiner* — Helen Chui
(74) *Attorney, Agent, or Firm* — Adam R. Stephenson, Ltd.

(57) ABSTRACT

Homeopathic compositions. Implementations of topical homeopathic compositions may include an actives portion including a plurality of active ingredients and a base including a plurality of inactive ingredients where the plurality of active ingredients include tinctures and/or homeopathic preparations of *Actaea spicata, Aesculus hippocastanum, Arnica montana, Atropa belladonna, Bellis perennis, Bryonia alba, Calendula officinalis,* Causticum, *Cimicifuga racemosa, Hypericum perforatum,* Kali Carbonicum, *Ledum palustre,* Lithium Carbonicum, *Rhododendron chrysanthum, Rhus toxicodendron, Ruta graveolens,* Salicylicum Acidum, and *Stellaria media* and one or more tinctures and/or homeopathic preparations selected from the group consisting of *Althaea officinalis, Caulophyllum thalictroides, Guaiacum, Rhamnus californica,* or any combination thereof.

12 Claims, No Drawings

HOMEOPATHIC FORMULATIONS

BACKGROUND

1. Technical Field

Aspects of this document relate generally to compositions used in homeopathic treatment of symptoms, diseases, and injuries.

2. Background Art

A large number of plant and animal extracts and chemicals have been observed to, in diluted quantities, enable healing and reduction of symptoms associated with diseases and injuries of the human or animal body. Homeopathic compositions operate using dilute concentrations of substances that modify the frequency of the diluent and produce a corresponding response in the human or animal body when taken externally or internally. Homeopathic compositions have been described as being effective by delivering a small amount of a substance that in large quantities would create the symptom being observed thereby allowing the body to properly develop a response that ultimately is able to eliminate the cause of the symptom being observed. A wide variety of conditions are treated using homeopathic compositions, including pain reduction, swelling, inflammation, joint pain, and many others.

SUMMARY

Implementations of topical homeopathic compositions may include an actives portion including a plurality of active ingredients and a base including a plurality of inactive ingredients where the plurality of active ingredients include tinctures and/or homeopathic preparations of *Actaea spicata, Aesculus hippocastanum, Arnica montana, Atropa belladonna, Bellis perennis, Bryonia alba, Calendula officinalis*, Causticum, *Cimicifuga racemosa, Hypericum perforatum*, Kali Carbonicum, *Ledum palustre*, Lithium Carbonicum, *Rhododendron chrysanthum, Rhus toxicodendron, Ruta graveolens*, Salicylicum Acidum, and *Stellaria media* and one or more tinctures and/or homeopathic preparations selected from the group consisting of *Althaea officinalis, Caulophyllum thalictroides, Guaiacum, Rhamnus californica*, or any combination thereof.

Implementations of topical homeopathic formulations may include one, all, or any of the following:

The base may include acrylates/C-10-30 alkyl acrylate crosspolymer, colloidal silver, citric acid, fulvic liquid minerals, potassium sorbate, water, sodium hydroxide, and vegetable glycerin (USP).

The water may be purified bio-photonic water and/or positively charged acidic water.

The actives portion may be about 80% by weight and the base may be about 20% by weight.

The actives portion may further include tinctures and/or homeopathic preparations selected from the group consisting of *Aconitum napellus*, Calcarea Carbonica, Kali Muriaticum, *Mezereum officinarum, Phytolacca decandra, Staphysagria*, or any combination thereof.

The potency of each one of the plurality of active ingredients included in the actives portion may be one of between about tincture to about 100x, between about 1 C to about 30 C, or about LM-1 to about LM-3.

The potency of each one of the plurality of active ingredients included in the actives portion may be 8x.

Implementations of a topical spray homeopathic formulation may include an actives portion including a plurality of active ingredients and a base including a plurality of inactive ingredients where the plurality of active ingredients include tinctures and/or homeopathic preparations of *Aesculus hippocastanum, Apis mellifica, Arnica montana, Atropa belladonna, Bryonia alba, Calendula officinalis*, Causticum, *Equisetum arvense, Hypericum perforatum*, Lithium Carbonicum, *Mezereum officinarum, Stellaria media, Symphytum officinale, Urtica urens*, and *Veratrinum* and one or more tinctures and/or homeopathic preparations selected from the group consisting of *Althaea officinalis, Anagallis arvensis, Cantharis, Nerium oleander, Sabina, Salix Alba, Staphysagria*, or any combination thereof.

Implementations of topical spray homeopathic formulations may include one, all, or any of the following:

The base may include acrylates/C-10-30 alkyl acrylate crosspolymer, vegetable glycerin, colloidal silver, citric acid, fulvic liquid minerals, potassium sorbate, water, and sodium hydroxide.

The actives portion may be about 85% by weight and the base may be about 15% by weight.

The actives portion may further include tinctures and/or homeopathic preparations selected from the group consisting of *Bellis Perennis*, Chamomilla, *Dolichos Pruriens*, Kali Muriaticum, *Verbascum*, or any combination thereof.

The potency of each one of the plurality of active ingredients comprised in the actives portion may be one of between about tincture to about 100x, between about 1 C to about 30 C, or about LM-1 to about LM-3.

The potency of each one of the plurality of active ingredients included in the actives portion may be 8x.

Implementations of an oral spray or bottle containing a dispensing dropper homeopathic formulation may include an actives portion including a plurality of active ingredients and a base including a plurality of inactive ingredients where the plurality of active ingredients include tinctures and/or homeopathic preparations of *Aconitum napellus, Actaea Spicata, Arnica montana, Bellis Perennis*, Calcarea Carbonica, Calcarea Fluorica, Causticum, *Cimicifuga racemosa*, Formicum Acidum, *Hypericum perforatum*, Kali Carbonicum, *Ledum palustre, Phytolacca Decandra, Pulsatilla nigricans, Rhododendron chrysanthum, Rhus toxicodendron, Ruta graveolens*, Salicylicum Acidum, and *Stellaria media* and one or more tinctures and/or homeopathic preparations selected from the group consisting of *Caulophyllum thalictroides, Guaiacum*, Lithium Carbonicum, *Rhamnus Californica*, Zincum Valerianum or any combination thereof.

Implementations of an oral spray or bottle containing a dispensing dropper homeopathic formulation may include one, all, or any of the following:

The base may include citric acid, fulvic liquid minerals, potassium sorbate, colloidal silver, and water.

The actives portion may be about 90% by weight and the base is about 10% by weight.

The actives portion further comprises tinctures and/or homeopathic preparations selected from the group consisting of Kali Muriaticum, Magnesia Phosphorica, *Mezereum Officinarum, Staphysagria, Verbascum*, or any combination thereof.

The potency of each one of the plurality of active ingredients included in the actives portion may be one of between about tincture to about 100x, between about 1 C to about 30 C, or about LM-1 to about LM-3.

The potency of each one of the plurality of active ingredients included in the actives portion may be 8x, 16x, and LM-1

DESCRIPTION

This disclosure, its aspects and implementations, are not limited to the specific components or assembly procedures disclosed herein. Many additional components and preparation procedures known in the art consistent with the intended homeopathic formulations and/or preparation procedures for a homeopathic formulation will become apparent for use with particular implementations from this disclosure. Accordingly, for example, although particular implementations are disclosed, such implementations and implementing components may comprise any shape, size, style, type, model, version, measurement, concentration, material, quantity, dilution and/or the like as is known in the art for such homeopathic formulations and implementing components, consistent with the intended operation.

Conventional topical analgesic preparations used for the temporary relief of the symptoms of minor aches, pains, and stiffness of muscle and joint, associated with arthritis, rheumatism, inflammation, simple backache, minor athletic injuries, sprains and strains, bumps and bruises, utilize counterirritants to create a hot, cool, or hot and cool sensation on the surface of the skin. Typical components of such preparations include capsaicin, wintergreen (methyl salicylate), and camphor and menthol. Other products address the symptoms of pain and related issues through vasodilation utilizing components like histamine dihydrochloride to increase blood flow to the applied area. The use of counterirritants can pose the risk of burning the skin when applied topically, and the repeated use of drugs such as salicylates may increase the risk of developing allergic reactions.

Homeopathy operates on a different principle than conventional over-the-counter preparations. Those solutions that are most concentrated in a particular component are considered least potent, while those that are least concentrated in a particular component are most potent. Based on the general principle of treating like with like, homeopathic preparations work using components that in large doses would create symptoms like those the patient is currently experiencing. However, by deliberately applying sequentially highly diluted or "potentized" preparations of these same components through a process called "succussion," the patient's body can be stimulated to take the actions needed to eliminate the symptoms associated with the disease and help facilitate the healing needed to recover from an injury. Each component of a homeopathic mixture is made from a plant, chemical compound, or animal in the form of a tincture at a specified concentration. The tincture is then sequentially diluted or succussed to a desired dilution to form a homeopathic preparation. Homeopathic ingredients that have been highly diluted are also referred to as high potency. Ultra high dilutions that may be used could produce results in which it may be physically impossible for a single molecule from the original component to be present in the solution applied. Homeopaths may refer to the process of succussing a tincture as establishing the frequency of the solution and using the resulting frequency of the solution to work with the body to provoke a healing response.

Dr. Samuel Hahnemann (1755-1843), a German physician considered by many to be the father of Homeopathy, believed that human beings have a capacity for healing themselves and that the symptoms of disease reflect the individual's struggle to overcome their illness. He discovered the principle that, what a particular substance could cause in the way of symptoms, it could also cure. Based on this understanding, Hahnemann proposed the "Law of Similars." In other words, if someone has certain symptoms, then regardless of the disease involved, taking a medicine that causing the same symptoms but highly diluted would produce opposite symptoms. In homeopathic medicine, this later became known as the "law of Infinitesimals." Homeopathic medicines and substances are considered by homeopaths to act as remedies by creating informational energy, stimulating the internal vital force, and thereby initiating an immune and healing response within the body to heal itself. In practice, while little or no side adverse side effects may be observed because of the dilution, a strong positive effect can be seen as the frequency of the solution works with the body.

Several different dilution scales are used in homeopathy to describe the end concentration of a given homeopathic preparation for a particular component. The centesimal or C scale is based on diluting by a factor of 100 at each stage. For example, to create a 1 C solution, 99 drops of diluent would be added to 1 drop of a tincture of the component. To create a 2 C solution, 99 drops of diluent would be added to 1 drop of a 1 C solution of the component. The decimal or D scale is based on diluting by a factor of 10 at each stage, or by adding 9 drops of diluent to 1 drop of tincture to create a 1× or 1 D solution. A 100× solution would be created by starting with a 1× solution and then repeating the process of taking one drop of the last dilution and adding 9 more drops of diluents to it 9 additional times. This type of dilution is base 10 logarithmic in scale. The quintamillesimal (Q) or LM scale is the process of creating a dilution of 1:50,000 in the first dilution. Accordingly, an LM-1 homeopathic preparation is prepared by sequentially succussing one drop of tincture with 49,999 drops of diluent. In practice, homeopathic preparations of given components range in dilution from tincture to 400× on the Decimal scale, tincture to 200 C on the C scale, and LM-1 to LM-3 on the LM scale.

The observed effectiveness of a given homeopathic preparation can depend upon the method used to administer it to the patient. For example, lower potency (higher concentration) homeopathic ingredients appear to have better results when used as a topical treatment application when compared to high potency ingredients. In contrast, high potency homeopathic ingredients work well when administered orally or internally. A potential problem with administering lower potency homeopathic preparations such as tinctures, 1×, 2× and 3× dilutions topically is that homeopathic ingredients are cut with ethyl alcohol as a preservative during the preparation process for further dilution to increase potency. As a result, tinctures and 1× potencies can contain between about 30 to about 60% ethyl alcohol. This high concentration of ethanol may be necessary to prevent bacterial growth while still retaining the benefit of the active ingredient. Low potency ingredients may work well when the benefit of the ingredient is not necessarily being used in the homeopathic capacity of like curing like, but is being used like a conventional medicine. However, if a homeopathic ingredient is used in lower potency where the application of the homeopathic ingredient is intended to operate homeopathically based on the principle of like curing like, then low potency application of those ingredients could pose a potential health risk to the skin due to the high concentration of the particular component in what is being applied to the skin.

Low potency ingredients may also present challenges when compared to high potency mixtures in that they tend to be less stable and characteristically have a much shorter shelf life. High potency ingredients, due to the very low concentration of ethanol and/or high amount of purified water diluent, tend to perform better in terms of stability and longer shelf life. Another challenge from the homeopath's perspective with low potency homeopathic preparations is that although they may perform well topically, they may also lack the ability to affect tissues deeper in the body. When a solution is prepared for the purpose of homeopathic topical application, a strategy is to blend in both low and high potency ingredients together (i.e., include both a 1× preparation and a 20× preparation of the same component in the same product) to provide a dual benefit. This may not be as safe when strictly using higher potency ingredients, however, when the solution is to be administered to younger people who will be more sensitive to the effects of the lower potency ingredients unless the monograph calls for tincture external use, where low dilutions can provide a benefit for a particular ingredient. Such monographed ingredient can provide a benefit for both low and high dilutions.

The various components included in implementations of homeopathic preparations disclosed in this document are selected from those officially listed in the Homeopathic Pharmacopoeia of the United States (HPUS). A description of the specific symptoms each of the components disclosed in this document may work to remedy may be found in William Boericke, M.D., *Materia Medica*, 9$^{th}$ Edition (1927), the relevant disclosures of which for each component are hereby incorporated herein by reference. Table 1 is a listing of all active ingredients (components) that may be used in the various preparation implementations disclosed in this document along with the range of dilutions that may be utilized for each. In this table, tincture refers to the mother tincture as defined in the HPUS.

TABLE 1

Active Ingredients

| Component | Dilution Range |
|---|---|
| Aconitum napellus | Tinct. - 100×, 1C-30C, LM-1 to LM-3 |
| Actaea spicata | Tinct. - 100×, 1C-30C, LM-1 to LM-3 |
| Aesculus hippocastanum | Tinct. - 100×, 1C-30C, LM-1 to LM-3 |
| Althaea officinalis | Tinct. - 100×, 1C-30C, LM-1 to LM-3 |
| Anagallis arvensis | Tinct. - 100×, 1C-30C, LM-1 to LM-3 |
| Apis mellifica | Tinct. - 100×, 1C-30C, LM-1 to LM-3 |
| Arnica montana | Tinct. - 100×, 1C-30C, LM-1 to LM-3 |
| Atropa belladonna | Tinct. - 100×, 1C-30C, LM-1 to LM-3 |
| Bellis perennis | Tinct. - 100×, 1C-30C, LM-1 to LM-3 |
| Bryonia alba | Tinct. - 100×, 1C-30C, LM-1 to LM-3 |
| Calcarea Carbonica | Tinct. - 100×, 1C-30C, LM-1 to LM-3 |
| Calcarea Fluorica | Tinct. - 100×, 1C-30C, LM-1 to LM-3 |
| Calendula officinalis | Tinct. - 100×, 1C-30C, LM-1 to LM-3 |
| Cantharis | Tinct. - 100×, 1C-30C, LM-1 to LM-3 |
| Caulophyllum thalictroides | Tinct. - 100×, 1C-30C, LM-1 to LM-3 |
| Causticum | Tinct. - 100×, 1C-30C, LM-1 to LM-3 |
| Chamomilla | Tinct. - 100×, 1C-30C, LM-1 to LM-3 |
| Cimicifuga racemosa | Tinct. - 100×, 1C-30C, LM-1 to LM-3 |
| Dolichos Pruriens | Tinct. - 100×, 1C-30C, LM-1 to LM-3 |
| Equisetum arvense | Tinct. - 100×, 1C-30C, LM-1 to LM-3 |
| Formicum Acidum | Tinct. - 100×, 1C-30C, LM-1 to LM-3 |
| Guaiacum | Tinct. - 100×, 1C-30C, LM-1 to LM-3 |
| Hypericum perforatum | Tinct. - 100×, 1C-30C, LM-1 to LM-3 |
| Kali Carbonicum | Tinct. - 100×, 1C-30C, LM-1 to LM-3 |
| Kali Muriaticum | Tinct. - 100×, 1C-30C, LM-1 to LM-3 |
| Ledum palustre | Tinct. - 100×, 1C-30C, LM-1 to LM-3 |
| Lithium Carbonicum | Tinct. - 100×, 1C-30C, LM-1 to LM-3 |
| Magnesia Phosphorica | Tinct. - 100×, 1C-30C, LM-1 to LM-3 |
| Mezereum officinarum | Tinct. - 100×, 1C-30C, LM-1 to LM-3 |
| Nerium oleander | Tinct. - 100×, 1C-30C, LM-1 to LM-3 |
| Phytolacca decandra | Tinct. - 100×, 1C-30C, LM-1 to LM-3 |
| Pulsatilla nigricans | Tinct. - 100×, 1C-30C, LM-1 to LM-3 |

TABLE 1-continued

Active Ingredients

| Component | Dilution Range |
|---|---|
| Rhamnus californica | Tinct. - 100×, 1C-30C, LM-1 to LM-3 |
| Rhododendron chrysanthum | Tinct. - 100×, 1C-30C, LM-1 to LM-3 |
| Rhus toxicodendron | Tinct. - 100×, 1C-30C, LM-1 to LM-3 |
| Ruta graveolens | Tinct. - 100×, 1C-30C, LM-1 to LM-3 |
| Sabina | Tinct. - 100×, 1C-30C, LM-1 to LM-3 |
| Salicylicum Acidum | Tinct. - 100×, 1C-30C, LM-1 to LM-3 |
| Salix Alba | Tinct. - 100×, 1C-30C, LM-1 to LM-3 |
| Staphysagria | Tinct. - 100×, 1C-30C, LM-1 to LM-3 |
| Stellaria media | Tinct. - 100×, 1C-30C, LM-1 to LM-3 |
| Symphytum officinale | Tinct. - 100×, 1C-30C, LM-1 to LM-3 |
| Urtica urens | Tinct. - 100×, 1C-30C, LM-1 to LM-3 |
| Veratrinum | Tinct. - 100×, 1C-30C, LM-1 to LM-3 |
| Verbascum | Tinct. - 100×, 1C-30C, LM-1 to LM-3 |
| Zincum Valerianum | Tinct. - 100×, 1C-30C, LM-1 to LM-3 |

A wide variety of combinations of potential active ingredients at desired potencies are possible using the list of ingredients and dilutions listed in Table 1. In this document, various implementations of a topical gel preparation, a topical spray preparation, and of an oral spray and/or bottle containing a dispensing dropper preparation are disclosed. The examples provided of each implementation are for the exemplary purposes of this disclosure. Those of ordinary skill in the art will readily be able to create additional implementations using the principles disclosed herein.

Table 2 illustrates the actives portion of an implementation of a topical gel preparation. In the implementation in the table, the each preparation is derived from an about 40% ethanol tincture solution of the whole plant, animal, or the chemical included.

TABLE 2

Actives Implementation 1

| Active Ingredients (HPUS) | Dilution | % of Weight of Actives Portion |
|---|---|---|
| Actaea spicata | 8× | 3.632% |
| Aesculus hippocastanum | 8× | 3.632% |
| Althaea officinalis | 8× | 3.632% |
| Arnica montana | 8× | 3.632% |
| Atropa belladonna | 8× | 3.632% |
| Bellis perennis | 8× | 3.632% |
| Bryonia alba | 8× | 3.632% |
| Calendula officinalis | 8× | 3.632% |
| Caulophyllum thalictroides | 8× | 3.632% |
| Causticum | 8× | 3.632% |
| Cimicifuga racemosa | 8× | 3.632% |
| Guaiacum | 8× | 3.632% |
| Hypericum perforatum | 8× | 3.632% |
| Kali Carbonicum | 8× | 3.632% |
| Ledum palustre | 8× | 3.632% |
| Lithium Carbonicum | 8× | 3.632% |
| Rhamnus californica | 8× | 3.632% |
| Rhododendron chrysanthum | 8× | 3.632% |
| Rhus toxicodendron | 8× | 3.632% |
| Ruta graveolens | 8× | 3.632% |
| Salicylicum Acidum | 8× | 3.632% |
| Stellaria media | 8× | 3.632% |

In various implementations, the Actives portion of the gel may constitute about 80% of the total weight of the gel, and in the implementation disclosed in Table 2, about 79.914% of the total weight of the gel. As used herein, "active" ingredients refers to those required by the U.S. Food and Drug Administration to be disclosed as being added for their pharmaceutical effect. The various inactive ingredients can also provide health benefits along with accomplishing their various other purposes, which may include, by non-limiting example, thickening, gelling, preserving, colorizing, odorizing, deodorizing, decolorizing, moisture retaining, drying, and any other desired function. Table 3 demonstrates an implementation of the inactive ingredients included in the base:

TABLE 3

Base Implementation 1

| Inactive Ingredients | % of Weight of Base |
| --- | --- |
| Purified water | 8.747% |
| Fulvic Liquid Minerals | 8.747% |
| Vegetable Glycerin (USP) | 1.5% |
| Acrylates/C-10-30 Alkyl Acrylate Crosspolymer | 0.5% |
| Sodium Hydroxide | 0.5% |
| Potassium Sorbate | 0.08% |
| Citric Acid | 0.006% |
| Colloidal Silver | 0.006% |

In various implementations, the base portion may be about 20% of the total weight of the topical gel, and in the implementation illustrated in Table 3, about 20.086% of the total weight of the gel. The acrylates/C-10-30 alkyl acrylate crosspolymer (the International Nomenclature Cosmetic ingredient (INCI) name) is a polymer gel designed to contain extremely low levels of benzene-containing residual solvent, in the range of 0.5 ppm. Such a polymer gel may exhibit rapid wetting properties not requiring agitation, high thickening efficiency, improved electrolyte tolerance, excellent clarity in applications, and superior aesthetic performance, depending upon the implementation selected. Implementations of such a polymer gel are marketed under the trade name CARBOPOL® Ultrez 21 Polymer by Lubrizol Advanced Materials of Cleveland, Ohio. Many conventional polymer gels are specified to contain 1000 ppm of residual benzene, which while within the limits set by the current edition of the United States Pharmacopoeia/National Formulary (USP/NF) for topical use, has been judged to be too high in many European countries, where the use of these polymer gels has been banned.

The use of sodium hydroxide as an emulsifier to buffer the gel base to enable thickening of the polymer gel is in contrast with many conventional gels which utilize triethanolamine, which contains amines which are subjects of concern in the alternative health care industry in the U.S. and Europe. Colloidal silver solution is utilized as an antimicrobial agent in the base. In particular implementations, the colloidal silver solution may be that marketed under the trade name BIO-ACTIVE SILVER HYDROSOL™ by Natural Immunogenics, Inc, of Pompano Beach, Fla. Because of the very small size of the particles of silver contained in this particular implementation of a silver hydrosol solution, toxicity issues related to the use of other conventional colloidal silver products can be avoided. The use of the silver hydrosol is in contrast with conventional gels which utilize methylparaben and other parabens to act as preservatives and anti-microbial agents.

In particular implementations, the purified water utilized in implementations of the base may be purified bio-photonic water or positively charged acidic water. Bio-photonic water may be processed using various filters that assist with aligning the water molecules into a hexagonal shape and enhancing the number of bio-photons present. Implementations of such filters may be those marketed under the trade name HEXAHEDRON 999 by E. Excelex of St-Ambroise-de-Kildare of Quebec, Canada. Implementations of such filters may include various internal blades, quartz crystals, minerals, gold powder, and internal flow structure that allows for the reprogramming of the hexagonal structure of the water, creation of a unified field within the water molecules, and increasing the amount of bio-photons present in the water as water flows through the filter. Water filtered using such filter implementations is referred to as purified bio-photonic water. Positively charged acidic water is processed through a device in which water flows through a charcoal silver filter and then through an anode chamber within the device which serves to positive charge the with hydrogen ions.

The fulvic minerals included in implementations of bases disclosed in this document may be any of various compositions extracted from fulvic mineral bases. In particular implementations, the fulvic liquid mineral composition may include 73 trace minerals extracted using a supplier proprietary process that performs the extraction from a fulvic acid containing mineral base resulting in a liquid that is slightly alkaline rather than acidic. Without being bound by any theory, the inclusion of the fulvic liquid minerals will further potentiate the activity of the various homeopathic preparations included as active ingredients in the actives portion, although the fulvic is liquid minerals are listed in the inactives portion.

While the use of specific inactive ingredients is described above and in other descriptions of base implementations disclosed in this document, these disclosures are for the exemplary purposes of this disclosure only. Accordingly, base implementations that may be utilized may include, one, all, or any of the various inactive ingredients disclosed in this document in any desired ratio in order to produce, by non-limiting example, a desired viscosity, a desired dry time on the skin, a desired taste, a desired shelf life, a desired biological activity, a desired potentiation of the homeopathic activity of the active ingredients, or any other desired characteristic or property of a gel, spray, liquid, or solid homeopathic preparation. In particular implementations ethanol may be added to the base of topical gel implementations in weight percentages between about 0.2% to about 3% to aid in enhancing the drying of the gel on the surface of the skin after application and/or to achieve a desired viscosity of the gel at the time of application. A wide variety of base implementations may be constructed using the principles disclosed in this document.

To prepare the topical homeopathic preparation, the actives portion and the base portion may be blended together, with about 80% of the weight of the final preparation coming from the actives portion and about 20% of the weight of the final preparation coming from the inactive ingredients in the base. In particular implementations, about 79.914% of the weight of the final preparation comes from the actives portion and about 20.086% of the weight comes from the inactive ingredients in the base. In particular implementations, the purified water may be processed as described in this document prior to be blended to create bio-photonic water or positively charged acidic water. In other implementations, the purified water may be mixed with the fulvic liquid minerals prior to processing with the filter, enabling creation of the bio-photonic water and additional enhancement of the potency of the fulvic minerals to enable greater potentiation of the activity of the actives in the actives portion of the final solution. During the blending process and afterward, avoiding high speed blending, violent agitation, direct sunshine, high temperatures (greater than 80 F/26 C), x-rays, and electromagnetic fields may be preferable to avoid any reduction in the potency of the active ingredients in the topical preparation.

The final composition may be packaged in an airless pump bottle configured to aid in dispensing by those suffering from limited dexterity and/or painful mobility. The pump bottle may have a volume of 50 ml in particular implementations. Such airless pump bottles may be designed to be incapable of aspirating the gel back into the tube because of an internal piston which, when depressed, is configured to eliminate the likelihood of the introduction of any contamination into the preparation. The pump bottle may also include a tip that self-seals after being depressed over the end of the bottle. A wide variety of packaging methods may also be employed, including, by non-limiting example, packing in plastic tubes, metallic tubes, jars, automatic dispensing tubes, and any other packaging material and system capable of preserving the potentiation of the topical solution. The blending and packaging processes will be performed in a FDA approved facility with a certified Good Manufacturing Practices (cGMP) rating.

The topical gel preparation may be used by adults and children 2 years of age or older. To use, the patient may clean the affected area and then gently apply a thin layer of the gel sufficient to cover the entire affected area. This may take place immediately at the onset of pain symptoms or afterward. Dosing may be limited to no more than 6 applications daily or every 15 minutes for the first hour after pain occurs. Use with wounds or damaged skin may not be recommended, as well as if symptoms persist beyond 7 days or reoccur after clearing up after few days or if rash or allergic reactions begin to appear.

Several other active ingredients may be substituted for specific active ingredients included in the implementation of Table 2. The following ingredients may be substituted to create the lists of active ingredients set forth in Implementations 2-14 of the active ingredients set forth in Table 4: *Aconitum napellus*, Calcarea Carbonica, Kali Muriaticum, *Mezereum officinarum*, *Phytolacca decandra*, and *Staphysagria* as indicated in bold type (all as set forth in the HPUS). In these implementations, the substituted ingredients are also included at a dilution of 8× and since the total number of active ingredients remains the same, each is substituted in at the same weight percent as the original ingredient.

TABLE 4

| Implementation 2 | Implementation 3 |
|---|---|
| Aconitum napellus | Aconitum napellus |
| Actaea spicata | Actaea spicata |
| Aesculus hippocastanum | Aesculus hippocastanum |
| Althaea officinalis | Althaea officinalis |
| Arnica montana | Arnica montana |
| Bellis perennis | Bellis perennis |
| Calcarea Carbonica | Calendula officinalis |
| Calendula officinalis | Caulophyllum thalictroides |
| Caulophyllum thalictroides | Causticum |
| Causticum | Cimicifuga racemosa |
| Cimicifuga racemosa | Guaiacum |
| Guaiacum | Hypericum perforatum |
| Hypericum perforatum | Kali Carbonicum |
| Kali Carbonicum | Kali Muriaticum |
| Ledum palustre | Ledum palustre |
| Lithium Carbonicum | Lithium Carbonicum |
| Rhamnus californica | Rhamnus californica |
| Rhododendron chrysanthum | Rhododendron chrysanthum |
| Rhus toxicodendron | Rhus toxicodendron |
| Ruta graveolens | Ruta graveolens |
| Salicylicum Acidum | Salicylicum Acidum |
| Stellaria media | Stellaria media |

TABLE 4-continued

| Implementation 4 | Implementation 5 |
|---|---|
| Actaea spicata | Actaea spicata |
| Aesculus hippocastanum | Aesculus hippocastanum |
| Althaea officinalis | Althaea officinalis |
| Arnica montana | Arnica montana |
| Bellis perennis | Bellis perennis |
| Calcarea Carbonica | Calendula officinalis |
| Calendula officinalis | Caulophyllum thalictroides |
| Caulophyllum thalictroides | Causticum |
| Causticum | Cimicifuga racemosa |
| Cimicifuga racemosa | Guaiacum |
| Guaiacum | Hypericum perforatum |
| Hypericum perforatum | Kali Carbonicum |
| Kali Carbonicum | Kali Muriaticum |
| Ledum palustre | Ledum palustre |
| Lithium Carbonicum | Lithium Carbonicum |
| Phytolacca decandra | Phytolacca decandra |
| Rhamnus californica | Rhamnus californica |
| Rhododendron chrysanthum | Rhododendron chrysanthum |
| Rhus toxicodendron | Rhus toxicodendron |
| Ruta graveolens | Ruta graveolens |
| Salicylicum Acidum | Salicylicum Acidum |
| Stellaria media | Stellaria media |

| Implementation 6 | Implementation 7 |
|---|---|
| Actaea spicata | Actaea spicata |
| Aesculus hippocastanum | Aesculus hippocastanum |
| Althaea officinalis | Althaea officinalis |
| Arnica montana | Arnica montana |
| Atropa belladonna | Atropa belladonna |
| Bellis perennis | Bellis perennis |
| Calcarea Carbonica | Calendula officinalis |
| Calendula officinalis | Caulophyllum thalictroides |
| Caulophyllum thalictroides | Causticum |
| Causticum | Cimicifuga racemosa |
| Cimicifuga racemosa | Guaiacum |
| Guaiacum | Hypericum perforatum |
| Hypericum perforatum | Kali Carbonicum |
| Kali Carbonicum | Kali Muriaticum |
| Ledum palustre | Ledum palustre |
| Lithium Carbonicum | Lithium Carbonicum |
| Rhamnus californica | Rhamnus californica |
| Rhododendron chrysanthum | Rhododendron chrysanthum |
| Rhus toxicodendron | Rhus toxicodendron |
| Ruta graveolens | Ruta graveolens |
| Salicylicum Acidum | Salicylicum Acidum |
| Stellaria media | Stellaria media |

| Implementation 8 | Implementation 9 |
|---|---|
| Actaea spicata | Actaea spicata |
| Aesculus hippocastanum | Aesculus hippocastanum |
| Althaea officinalis | Althaea officinalis |
| Arnica montana | Arnica montana |
| Bellis perennis | Bellis perennis |
| Bryonia alba | Bryonia alba |
| Calendula officinalis | Calendula officinalis |
| Caulophyllum thalictroides | Caulophyllum thalictroides |
| Causticum | Causticum |
| Cimicifuga racemosa | Cimicifuga racemosa |
| Guaiacum | Guaiacum |
| Hypericum perforatum | Hypericum perforatum |
| Kali Carbonicum | Kali Carbonicum |
| Ledum palustre | Kali Muriaticum |
| Lithium Carbonicum | Ledum palustre |
| Phytolacca decandra | Lithium Carbonicum |
| Rhamnus californica | Rhamnus californica |
| Rhododendron chrysanthum | Rhododendron chrysanthum |
| Rhus toxicodendron | Rhus toxicodendron |
| Ruta graveolens | Ruta graveolens |
| Salicylicum Acidum | Salicylicum Acidum |
| Stellaria media | Stellaria media |

| Implementation 10 | Implementation 11 |
|---|---|
| Aconitum napellus | Actaea spicata |
| Actaea spicata | Aesculus hippocastanum |
| Aesculus hippocastanum | Althaea officinalis |

TABLE 4-continued

| | |
|---|---|
| Althaea officinalis | Arnica montana |
| Arnica montana | Bellis perennis |
| Bellis perennis | Calcarea Carbonica |
| Calendula officinalis | Calendula officinalis |
| Caulophyllum thalictroides | Caulophyllum thalictroides |
| Causticum | Causticum |
| Cimicifuga racemosa | Cimicifuga racemosa |
| Guaiacum | Guaiacum |
| Hypericum perforatum | Hypericum perforatum |
| Kali Carbonicum | Kali Carbonicum |
| Ledum palustre | Kali Muriaticum |
| Lithium Carbonicum | Ledum palustre |
| Phytolacca decandra | Lithium Carbonicum |
| Rhamnus californica | Rhamnus californica |
| Rhododendron chrysanthum | Rhododendron chrysanthum |
| Rhus toxicodendron | Rhus toxicodendron |
| Ruta graveolens | Ruta graveolens |
| Salicylicum Acidum | Salicylicum Acidum |
| Stellaria media | Stellaria media |
| Implementation 12 | Implementation 13 |
| Actaea spicata | Actaea spicata |
| Aesculus hippocastanum | Aesculus hippocastanum |
| Althaea officinalis | Althaea officinalis |
| Arnica montana | Arnica montana |
| Atropa belladonna | Atropa belladonna |
| Bryonia alba | Bellis perennis |
| Calendula officinalis | Bryonia alba |
| Caulophyllum thalictroides | Calendula officinalis |
| Causticum | Caulophyllum thalictroides |
| Cimicifuga racemosa | Causticum |
| Guaiacum | Cimicifuga racemosa |
| Hypericum perforatum | Guaiacum |
| Kali Carbonicum | Hypericum perforatum |
| Ledum palustre | Kali Carbonicum |
| Lithium Carbonicum | Ledum palustre |
| Rhamnus californica | Lithium Carbonicum |
| Rhododendron chrysanthum | Mezereum officinarum |
| Rhus toxicodendron | Rhamnus californica |
| Ruta graveolens | Rhododendron chrysanthum |
| Salicylicum Acidum | Ruta graveolens |
| Staphysagria | Salicylicum Acidum |
| Stellaria media | Stellaria media |

Implementation 14

Actaea spicata
Aesculus hippocastanum
Althaea officinalis
Arnica montana
Atropa belladonna
Bryonia alba
Calendula officinalis
Caulophyllum thalictroides
Causticum
Cimicifuga racemosa
Guaiacum
Hypericum perforatum
Kali Carbonicum
Ledum palustre
Lithium Carbonicum
Mezereum officinarum
Rhamnus californica
Rhododendron chrysanthum
Ruta graveolens
Salicylicum Acidum
Staphysagria
Stellaria media Implementations of a topical spray homeopathic composition may include the following active ingredients listed in Table 5 at the specified dilution and weight percent of the actives portion:

TABLE 5

Actives Implementation 15

| Active Ingredients (HPUS) | Dilution | % of Weight of Actives Portion |
|---|---|---|
| Aesculus hippocastanum | 8× | 3.8595% |
| Althaea officinalis | 8× | 3.8595% |
| Anagallis arvensis | 8× | 3.8595% |
| Apis mellifica | 8× | 3.8595% |
| Arnica montana | 8× | 3.8595% |
| Atropa belladonna | 8× | 3.8595% |
| Bryonia alba | 8× | 3.8595% |
| Calendula officinalis | 8× | 3.8595% |
| Cantharis | 8× | 3.8595% |
| Causticum | 8× | 3.8595% |
| Equisetum arvense | 8× | 3.8595% |
| Hypericum perforatum | 8× | 3.8595% |
| Lithium Carbonicum | 8× | 3.8595% |
| Mezereum Officinarum | 8× | 3.8595% |
| Nerium oleander | 8× | 3.8595% |
| Sabina | 8× | 3.8595% |
| Salix alba | 8× | 3.8595% |
| Staphysagria | 8× | 3.8595% |
| Stellaria media | 8× | 3.8595% |
| Symphytum Officinale | 8× | 3.8595% |
| Urtica Urens | 8× | 3.8595% |
| Veratrinum | 8× | 3.8595% |

In various implementations, the actives portion of the topical spray constitutes about 85% of the total weight of the topical spray. In the implementation disclosed in Table 5, the actives portion may constitute 84.9086% of the total weight of the topical spray. Table 6 demonstrates an implementation of the inactive ingredients included in the base:

TABLE 6

Base Implementation 2

| Inactive Ingredients | % of Weight of Base |
|---|---|
| Fulvic Liquid Minerals | 14.644% |
| Vegetable Glycerin (USP) | 0.21% |
| Acrylates/C-10-30 Alkyl Acrylate Crosspolymer | 0.07% |
| Sodium Hydroxide | 0.07% |
| Potassium Sorbate | 0.085% |
| Citric Acid | 0.0064% |
| Colloidal Silver | 0.006% |

In various implementations, the base portion may be about 15% of the total weight of the topical spray. In the implementation illustrated in Table 6, the base portion is 15.0914% of the total weight of the topical spray.

In implementations of the base, the same fulvic liquid minerals and colloidal silver may be utilized as were disclosed in the topical gel implementation. Because the liquid needed to create the spray may come primarily from the liquid included in the actives portion, there may be no need to add additional purified water. The fulvic liquid minerals may be processed through a bio-photonic water filter as part of the process of preparation. The effect of the fulvic liquid minerals may also be the same on the potentiation of the active ingredients as it was discussed with the topical gel implementation.

The spray implementation may be prepared by mixing the actives with the inactive ingredients and placing the resulting liquid composition in a bottle or other container capable of spraying the mixture out. The bottle or other container may be made of darkened or opaque materials to protect the mixture from light, and the same precautions listed for preparation of the topical gel may be observed. Like the topical gel, implementations of topical sprays will also be manufactured in a FDA approved facility with certified Good Manufacturing Practice (cGMP) ratings.

Implementations of the topical spray may be utilized by adults and children two years of age or older to treat a wide variety of symptoms and injuries, including minor pain, redness, sunburns, minor burns, and minor insect bites. The area to be treated is first cleaned and the topical spray is sprayed over the entire affected area immediately at the onset of pain or thereafter. The application of the spray may be limited to no more than 4 to 5 times daily. In particular situations, if the symptoms do not respond within the first 15 minutes of use, the application of the spray may be repeated. If the symptoms worsen, persist for more than 7 days, clear up and occur again within a few days, or if rash or other allergic reaction begins, use of the topical spray may be discontinued.

Several other active ingredients may be substituted for specific active ingredients included in the implementation of Table 5. The following ingredients may be substituted to create the lists of active ingredients set forth in Implementations 16-20 of the active ingredients set forth in Table 7: *Bellis perennis*, Chamomilla, *Dolichos pruriens*, Kali Muriaticum, and *Verbascum* as indicated in bold type (all as set forth in the HPUS). In these implementations, the substituted ingredients are also included at a dilution of 8× and since the total number of active ingredients remains the same, each is substituted in at the same weight percent as the original ingredient.

TABLE 7

| Implementation 16 | Implementation 17 |
|---|---|
| *Aesculus hippocastanum* | *Aesculus hippocastanum* |
| *Althaea officinalis* | *Althaea officinalis* |
| *Anagallis arvensis* | *Anagallis arvensis* |
| *Apis mellifica* | *Apis mellifica* |
| *Arnica montana* | *Arnica montana* |
|  | *Atropa belladonna* |
| *Calendula officinalis* | *Calendula officinalis* |
| *Cantharis* | *Cantharis* |
| Causticum | Causticum |
| Chamomilla |  |
|  | *Equisetum arvense* |
| *Equisetum arvense* | Lithium Carbonicum |
| Kali Muriaticum | Kali Muriaticum |
| Lithium Carbonicum | *Mezereum Officinarum* |
| *Mezereum Officinarum* | *Nerium oleander* |
| *Nerium oleander* | *Salix alba* |
| *Salix alba* | *Staphysagria* |
| *Stellaria media* | *Stellaria media* |
| *Symphytum Officinale* | *Symphytum Officinale* |
| *Urtica Urens* | *Urtica Urens* |
| *Veratrinum* | *Veratrinum* |
| Verbascum | Verbascum |

| Implementation 18 | Implementation 19 |
|---|---|
| *Aesculus hippocastanum* | *Aesculus hippocastanum* |
| *Althaea officinalis* | *Althaea officinalis* |
| *Anagallis arvensis* | *Anagallis arvensis* |
| *Apis mellifica* | *Apis mellifica* |
| *Arnica montana* | *Arnica montana* |
| *Calendula officinalis* | *Atropa belladonna* |
| *Cantharis* | *Bryonia alba* |
| Causticum | *Calendula officinalis* |
| Chamomilla | *Cantharis* |
| *Equisetum arvense* | Causticum |
| Kali Muriaticum |  |
| Lithium Carbonicum | *Equisetum arvense* |
| *Mezereum Officinarum* | Lithium Carbonicum |
| *Nerium oleander* | *Mezereum Officinarum* |
| Sabina | *Nerium oleander* |

TABLE 7-continued

| | |
|---|---|
| *Salix alba* | *Salix alba* |
| *Staphysagria* | *Staphysagria* |
| *Stellaria media* | *Stellaria media* |
| *Symphytum Officinale* | *Symphytum Officinale* |
| *Urtica Urens* | *Urtica Urens* |
| *Veratrinum* | *Veratrinum* |
| Verbascum | Verbascum |

| Implementation 20 |
|---|
| *Aesculus hippocastanum* |
| *Althaea officinalis* |
| *Anagallis arvensis* |
| *Apis mellifica* |
| *Arnica montana* |
| *Atropa belladonna* |
| *Calendula officinalis* |
| *Cantharis* |
| Causticum |
| *Equisetum arvense* |
| *Hypericum perforatum* |
| Kali Muriaticum |
| Lithium Carbonicum |
| *Mezereum Officinarum* |
| *Nerium oleander* |
| Sabina |
| *Salix alba* |
| *Stellaria media* |
| *Symphytum Officinale* |
| *Urtica Urens* |
| *Veratrinum* |

Implementations of an oral spray and/or a bottle containing a dispensing dropper composition adapted for use with a bottle containing a dropper which can be administered in a glass or bowl of water for consumption for both human and animals may include the following active ingredients listed in Table 8 at the specified dilution and weight percent of the actives portion:

TABLE 8

Actives Implementation 21

| Active Ingredients (HPUS) | Dilution in equal parts | % of Weight of Actives Portion |
|---|---|---|
| *Aconitum napellus* | 8×, 16×, LM-1 | 3.7460% |
| *Actaea spicata* | 8×, 16×, LM-1 | 3.7460% |
| *Arnica montana* | 8×, 16×, LM-1 | 3.7460% |
| *Bellis Perennis* | 8×, 16×, LM-1 | 3.7460% |
| Calcarea Carbonica | 8×, 16×, LM-1 | 3.7460% |
| Calcarea Fluorica | 8×, 16×, LM-1 | 3.7460% |
| *Caulophyllum thalictroides* | 8×, 16×, LM-1 | 3.7460% |
| Causticum | 8×, 16×, LM-1 | 3.7460% |
| *Cimicifuga racemosa* | 8×, 16×, LM-1 | 3.7460% |
| Formicum Acidum | 8×, 16×, LM-1 | 3.7460% |
| Guaiacum | 8×, 16×, LM-1 | 3.7460% |
| *Hypericum perforatum* | 8×, 16×, LM-1 | 3.7460% |
| Kali Carbonicum | 8×, 16×, LM-1 | 3.7460% |
| *Ledum palustre* | 8×, 16×, LM-1 | 3.7460% |
| Lithium Carbonicum | 8×, 16×, LM-1 | 3.7460% |
| *Phytolacca decandra* | 8×, 16×, LM-1 | 3.7460% |
| *Pulsatilla nigricans* | 8×, 16×, LM-1 | 3.7460% |
| *Rhamnus californica* | 8×, 16×, LM-1 | 3.7460% |
| *Rhododendron chrysanthum* | 8×, 16×, LM-1 | 3.7460% |
| *Rhus toxicodendron* | 8×, 16×, LM-1 | 3.7460% |
| *Ruta graveolens* | 8×, 16×, LM-1 | 3.7460% |
| Salicylicum Acidum | 8×, 16×, LM-1 | 3.7460% |
| *Stellaria media* | 8×, 16×, LM-1 | 3.7460% |
| Zincum Valerianum | 8×, 16×, LM-1 | 3.7460% |

Bottles containing dispensing droppers are used to enable the liquid in the bottle to be removed and dispensed into the patient's mouth directly or a cup or dish to be further diluted with additional water before being taken internally by a human or animal. In various implementations, the actives portion of the oral spray or bottle containing a dispensing dropper implementation may constitute about 90% of the total weight of the oral spray. In the implementation disclosed in Table 8, the actives portion contains about 89.9033% of the total weight of the oral spray or dropper bottle composition. Table 9 demonstrates an implementation of the inactive ingredients included in the base:

TABLE 9

Base Implementation 3

| Inactive Ingredients | % of Weight of Base |
| --- | --- |
| Fulvic Liquid Minerals | 9.996% |
| Potassium Sorbate | 0.09% |
| Citric Acid | 0.00675% |
| Colloidal Silver | 0.004% |

In various implementations, the base portion may be about 10% of the total weight of the oral spray. In this implementation, the base portion is about 10.0968% of the total weight of the combined oral spray or bottle containing a dispensing dropper composition.

In implementations of the base, the same fulvic liquid minerals and colloidal silver may be utilized as were disclosed in the topical gel implementation. In these implementations, the actual ratio of fulvic liquid minerals may range from about 10% to about 20% of the total spray by weight. As with the topical spray, because the liquid needed to create the oral spray may come primarily from the liquid included in the actives portion, there may be no need to add additional purified water. The fulvic liquid minerals may be run through a bio-photonic water filter as part of the process for the final solution. The effect of the fulvic liquid minerals may also be the same on the potentiation of the active ingredients as it was for the topical gel and topical spray implementations. Because three different dilutions or potencies of each active ingredient are used, multiple dynamics may be observed in the body's interaction with each active ingredient at each potency, particularly when the product is used for internal use with humans and animals.

The oral spray implementation may be prepared similarly to the topical spray implementation and be stored in a bottle or other container capable of spraying the mixture out or in a bottle containing a dispensing dropper which can be administered into a glass or bowl of water for consumption. The bottle or other container may be made of darkened or opaque materials to protect the mixture from light, and the same precautions listed for preparation of the topical gel and topical spray may be observed. In particular implementations, the bottle may be a two ounce translucent bottle. Like the topical gel and topical spray, implementations of oral sprays will also be manufactured in FDA approved facilities with certified Good Manufacturing Practice (cGMP) ratings.

Implementations of the oral spray or solution held in a bottle containing a dropper may be utilized by adults 18 years of age or older and children ages 12-17 to treat a wide variety of symptoms and injuries, including minor aches, pains, spasms and stiffness of joints associated with arthritis, rheumatism, simple backache, minor athletic injuries, sprains, and strains. Use with animals is done on a proportion basis as with humans, but calculated on the basis of weight. To use, the patient first may need to press the pump 4-5 times or until the pump is primed for a spray. The nozzle is then placed toward the patient's mouth and the pump pressed to release a spray. For adults ages 18 and older, three sprays into the mouth may be applied every 3 to 4 hours. For children age 12 to 17 years, the dosage may be two sprays into the mouth every 3 to 4 hours. If the pain symptoms do not respond to the first dose within 15 minutes, the dose may be repeated. The maximum dosage may be 6 doses per day. In various situations, this preparation may not be used on an ongoing basis beyond 10 days unless directed by a physician. If pain, ache, spasm, or stiffness persists or gets worse, or if new symptoms arise or an allergic reaction like those listed begins to occur, then use of the oral spray may need to be discontinued.

Several other active ingredients may be substituted for specific active ingredients included in the implementation of Table 8. The following ingredients may be substituted to create the lists of active ingredients set forth in Implementations 22-26 of the active ingredients set forth in Table 10: Kali Muriaticum, Magnesia Phosphorica, *Mezereum officinarum*, *Staphysagria*, and *Verbascum* as indicated in bold type (all as set forth in the HPUS). In these implementations, the substituted ingredients are also included at dilutions of 8×, 16×, and LM-1. Since the total number of active ingredients remains the same, each is substituted in at the same weight percent as the original ingredient.

TABLE 10

| Implementation 22 | Implementation 23 |
| --- | --- |
| *Aconitum napellus* | *Aconitum napellus* |
| *Actaea spicata* | *Actaea spicata* |
| *Arnica montana* | *Arnica montana* |
| Calcarea Carbonica | Calcarea Carbonica |
| Calcarea Fluorica | Calcarea Fluorica |
| *Caulophyllum thalictroides* | *Caulophyllum thalictroides* |
| Causticum | Causticum |
| *Cimicifuga racemosa* | *Cimicifuga racemosa* |
| *Guaiacum* | *Guaiacum* |
| *Hypericum perforatum* | *Hypericum perforatum* |
| Kali Carbonicum | Kali Carbonicum |
| Kali Muriaticum | Kali Muriaticum |
| *Ledum palustre* | *Ledum palustre* |
| Magnesia Phosphorica | Magnesia Phosphorica |
| *Mezereum officinarum* | *Phytolacca decandra* |
| *Phytolacca decandra* | *Rhamnus californica* |
| *Rhamnus californica* | *Rhododendron chrysanthum* |
| *Rhododendron chrysanthum* | *Rhus toxicodendron* |
| *Ruta graveolens* | *Ruta graveolens* |
| Salicylicum Acidum | Salicylicum Acidum |
| *Stellaria media* | *Staphysagria* |
| *Staphysagria* | *Stellaria media* |
| *Verbascum* | *Verbascum* |
| Zincum Valerianum | Zincum Valerianum |
| Implementation 24 | Implementation 25 |
| *Aconitum napellus* | *Aconitum napellus* |
| *Actaea spicata* | *Actaea spicata* |
| *Arnica montana* | *Arnica montana* |
| Calcarea Carbonica | Calcarea Carbonica |
| Calcarea Fluorica | Calcarea Fluorica |
| *Caulophyllum thalictroides* | *Caulophyllum thalictroides* |
| Causticum | Causticum |
| *Cimicifuga racemosa* | *Cimicifuga racemosa* |
| *Guaiacum* | *Guaiacum* |
| *Hypericum perforatum* | *Hypericum perforatum* |
| Kali Carbonicum | Kali Carbonicum |
| Kali Muriaticum | Kali Muriaticum |
| *Ledum palustre* | *Ledum palustre* |
| *Phytolacca decandra* | Lithium Carbonicum |
| *Pulsatilla nigricans* | *Phytolacca decandra* |
| *Rhamnus californica* | *Pulsatilla nigricans* |
| *Rhododendron chrysanthum* | *Rhamnus californica* |
| *Rhus toxicodendron* | *Rhododendron chrysanthum* |
| *Ruta graveolens* | *Rhus toxicodendron* |
| Salicylicum Acidum | *Ruta graveolens* |
| *Staphysagria* | Salicylicum Acidum |

TABLE 10-continued

| | |
|---|---|
| Stellaria media | Staphysagria |
| Verbascum | Stellaria media |
| Zincum Valerianum | Zincum Valerianum |

Implementation 26

Aconitum napellus
Actaea spicata
Arnica montana
Bellis Perennis
Calcarea Carbonica
Calcarea Fluorica
Caulophyllum thalictroides
Causticum
Cimicifuga racemosa
Guaiacum
Hypericum perforatum
Kali Carbonicum
Kali Muriaticum
Ledum palustre
Lithium Carbonicum
Phytolacca decandra
Pulsatilla nigricans
Rhamnus californica
Rhododendron chrysanthum
Rhus toxicodendron
Ruta graveolens
Salicylicum Acidum
Stellaria media
Zincum Valerianum In places where the description above refers to particular implementations of homeopathic preparations, it should be readily apparent that a number of modifications may be made without departing from the spirit thereof and that these implementations may be applied to other homeopathic preparations.

The invention claimed is:

1. A topical homeopathic formulation consisting of (a) an actives portion consisting of a plurality of active ingredients and (b) a base portion that is inactive ingredients, wherein the plurality of active ingredients consists of:
tinctures and/or homeopathic preparations of *Actaea spicata, Aesculus hippocastanum, Arnica montana, Atropa belladonna, Bells perennis, Bryonia alba, Calendula officinalis, Causticum, Cimicifuga racemosa, Hypericum perforatum*, Kali Carbonicum, *Ledum palustre*, Lithium Carbonicum, *Rhododendron chrysanthum, Rhus toxicodendron, Ruta graveolens*, Salicylicum Acidum, and *Stellaria media*; and
one or more tinctures and/or homeopathic preparations selected from the group consisting of *Althaea officinalis, Caulophyllum thalictroides, Guaiacum, Rhamnus californica*, and any combination thereof.

2. The formulation of claim 1, wherein the base consists of acrylates/C10-30 alkyl acrylate crosspolymer, colloidal silver, citric acid, fulvic liquid minerals, potassium sorbate, water, sodium hydroxide, and vegetable glycerin (USP).

3. The formulation of claim 2, wherein the water is purified bio-photonic water or positively charged acidic water.

4. The formulation of claim 1 wherein the actives portion is about 80% by weight of the total weight of the formulation and the base is about 20% by weight of the total weight of the formulation.

5. A topical homeopathic formulation consisting of (a) an actives portion consisting of a plurality of active ingredients and (b) a base portion that is inactive ingredients, wherein the plurality of active ingredients consists of:
tinctures and/or homeopathic preparations of *Actaea spicata, Aesculus hippocastanum, Arnica montana, Atropa belladonna, Bells perennis, Bryonia alba, Calendula officinalis, Causticum, Cimicifuga racemosa, Hypericum perforatum*, Kali Carbonicum, *Ledum palustre*, Lithium Carbonicum, *Rhododendron chrysanthum, Rhus toxicodendron, Ruta graveolens*, Salicylicum Acidum, and *Stellaria media*;
one or more tinctures and/or homeopathic preparations selected from the group consisting of *Althaea officinalis, Caulophyllum thalictroides, Guaiacum, Rhamnus californica*, and any combination thereof; and
one or more tinctures and/or homeopathic preparations selected from the group consisting of *Aconitum napellus*, Calcarea Carbonica, Kali Muriaticum, *Mezereum officinarum, Phytolacca decandra, Staphysagria*, and any combination thereof.

6. The formulation of claim 1, wherein the dilution of each one of the plurality of active ingredients in the actives portion is between tincture to 100×, between 1 C to 30 C, or between LM–1 to LM–3.

7. The formulation of claim 1, wherein the dilution of each one of the plurality of active ingredients in the actives portion is 8×.

8. The formulation of claim 5, wherein the dilution of each one of the plurality of active ingredients in the actives portion is between tincture to 100×, between 1 C to 30 C, or between LM–1 to LM–3.

9. The formulation of claim 5, wherein the dilution of each one of the plurality of active ingredients in the actives portion is 8λ.

10. The formulation of claim 5, wherein the base consists of acrylates/C10-30 alkyl acrylate crosspolymer, colloidal silver, citric acid, fulvic liquid minerals, potassium sorbate, water, sodium hydroxide, and vegetable glycerin (USP).

11. The formulation of claim 10, wherein the water is purified bio-photonic water or positively charged acidic water.

12. The formulation of claim 5, wherein the actives portion is about 80% by weight of the total weight of the formulation and the base is about 20% by weight of the total weight of the formulation.

* * * * *